United States Patent
Proksa

(10) Patent No.: US 8,050,385 B2
(45) Date of Patent: Nov. 1, 2011

(54) EVENT SHARING RESTORATION FOR PHOTON COUNTING DETECTORS

(75) Inventor: Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 168 days.

(21) Appl. No.: 12/523,998

(22) PCT Filed: Jan. 28, 2008

(86) PCT No.: PCT/IB2008/050294
§ 371 (c)(1),
(2), (4) Date: Jul. 22, 2009

(87) PCT Pub. No.: WO2008/093275
PCT Pub. Date: Aug. 7, 2008

(65) Prior Publication Data
US 2010/0025593 A1  Feb. 4, 2010

(30) Foreign Application Priority Data
Feb. 1, 2007  (EP) ..................................... 07101572

(51) Int. Cl.
*H05G 1/64* (2006.01)
*G01N 23/087* (2006.01)

(52) U.S. Cl. ..... 378/98.9; 378/5; 378/98.8; 250/370.08; 250/371

(58) Field of Classification Search ............. 378/5, 98.8, 378/98.9; 250/370.08, 371
See application file for complete search history.

(56) References Cited

U.S. PATENT DOCUMENTS

| | | | |
|---|---|---|---|
| 4,897,788 A | 1/1990 | King | |
| 5,574,758 A * | 11/1996 | Murakami et al. | 376/245 |
| 6,559,453 B2 * | 5/2003 | Lundqvist | 250/371 |
| 7,214,944 B2 * | 5/2007 | Rostaing et al. | 250/370.06 |
| 7,355,181 B2 * | 4/2008 | Amemiya et al. | 250/363.04 |
| 7,473,902 B2 * | 1/2009 | Spahn | 250/370.09 |
| 2003/0075685 A1 | 4/2003 | Yamakawa | |
| 2003/0138075 A1 * | 7/2003 | Sipila et al. | 378/19 |
| 2003/0160175 A1 | 8/2003 | Nygard et al. | |
| 2004/0124316 A1 | 7/2004 | Marron | |
| 2004/0264627 A1 * | 12/2004 | Besson | 378/5 |
| 2005/0111612 A1 | 5/2005 | Ikhlef et al. | |
| 2005/0201513 A1 | 9/2005 | Nukui et al. | |
| 2006/0086913 A1 | 4/2006 | Spahn | |

FOREIGN PATENT DOCUMENTS

| | | |
|---|---|---|
| EP | 1512376 A1 | 3/2005 |
| JP | 2007155360 A | 6/2007 |

* cited by examiner

*Primary Examiner* — Hoon Song
*Assistant Examiner* — Thomas R Artman

(57) ABSTRACT

Photon counting detectors may suffer from pulse sharing effects and fluorescence photon generation, which may lead to a degradation of the measured signals. According to an exemplary embodiment of the present invention, a detector unit is provided which is adapted for performing a coincidence detection and correction by comparing detection events of neighbouring cells, thereby providing for a coincidence identification followed by an individual coincidence correction. In order to reduce the number of coincidence detection and corresponding units per detector unit, a specific detector cell geometry may be applied.

19 Claims, 3 Drawing Sheets

EVENT SHARING RESTORATION FOR PHOTON COUNTING DETECTORS

The invention relates to the field of tomographic imaging. In particular, the invention relates to a detector unit for performing a coincidence detection and correction, an examination apparatus for examination of an object of interest, a method of examination of an object of interest, a computer-readable medium, a program element and a signal processing device.

Photon counting detectors with energy discrimination are a key component for future spectral computed tomography (CT) systems. Current detector designs based on cadmium/zinc/tellurium (CZT) as primary converter are designed for detecting and counting incoming photons, which interact with the CZT, thereby generating an electron cloud. The generated electrons are accelerated towards an anode array, resulting in a pulse.

There are two well-known effects that cause a degradation of the measured signals. The first is the so-called pulse sharing effect. If an X-ray photon hits the CZT somewhere between two anodes, the generated electrons might be shared between the two anodes. The electronic may interpret the signals as two independent events with shared energy. Another effect that causes a similar wrong interpretation may happen if the X-ray photon generates a so-called fluorescence photon. In such a case the energy of the X-ray photon is partly given to the fluorescence photon and the rest is deposed locally. The energy of the fluorescence photon is relatively high and there is high likelihood that it reaches a neighbour cell. Again, a single incoming X-ray photon may generate two signals with shared energy equivalents.

The likelihood of both effects may depend on the cell size. Larger cells may suffer less from both effects.

However, another severe challenge is to reach high count-rates. High count-rates may be realized with small cells, because the count workload is divided over more small cells with lower individual count-rate requirements. A compromise has to be found between these two competing requirements.

It would be desirable to have a reduced degradation of measured signals for a photo counting detector.

The invention provides a detector unit, an examination apparatus, a method of examination of an object of interest, a computer-readable medium, a program element and a signal processing device with the features according to the independent claims.

It should be noted that the following described exemplary embodiments of the invention apply also for the method of examination of the object of interest, for the computer-readable medium, for the program element and for the signal processing device.

According to a first aspect of the present invention, a detector unit for performing a coincidence detection and correction (CDC) is provided, the detector unit comprising a first detector cell adapted for detecting a first pulse resulting in first detection data and a second detector cell adapted for detecting a second pulse resulting in second detection data, and a coincidence detection and correction unit (CDC unit) coupled to the first and second detector cells and adapted for detecting a coincidence of the first and second pulses, wherein the coincidence detection and correction unit is further adapted for performing a correction of the first detection data, if a coincidence is detected.

In other words, the detector unit may comprise a plurality of detector cells which are adapted for detecting electric pulses resulting from incoming photons. Each detector cell may be coupled to a respective electronic unit, which, in turn, does not only watch the electric pulses detected by the respective detector cell, but also the pulses detected by neighbouring detector cells. In case the electronic unit detects a coincidence of two pulses which are detected by neighbouring cells, the detected data is corrected according to the coincidence. Such a correction may be performed by not counting the event in one cell and counting the event with an energy level of $e_1+e_2$ in the other cell (wherein $e_1$ is the energy detected in the first cell and $e_2$ is the energy detected in the second, neighbouring cell).

This may provide for a dedicated coincidence detection and correction and thus for a reduction of the effects of pulse sharing and fluorescence induced crosstalk.

According to another exemplary embodiment of the present invention, the detection of the coincidence is performed on the basis of an analysis of the first and second detection data.

For example, according to this exemplary embodiment, the characteristics of the underlying physical effects are analyzed. The specific characteristics are that the two pulses of a pulse sharing event are detected at the same time and have a similar pulse shape but perhaps different amplitudes. For fluorescence, the respective set of energies for the fluorescence event may be analyzed.

This may provide for an exact coincidence detection.

According to another exemplary embodiment of the present invention, the first detector cell is adapted for generating a first and a second measure corresponding to the first pulse, wherein the first measure corresponds to a first time of the first pulse and wherein the second measure corresponds to a first energy of the first pulse. Furthermore, the second detector cell is adapted for generating a third and a fourth measure corresponding to the second pulse, wherein the third measure corresponds to a second time of the second pulse and wherein the fourth measure corresponds to a second energy of the second pulse. The analysis is performed on the basis of the first, second, third and fourth measure.

Thus, for each pair of pulse detection events (each event being detected at one detector cell) the detection times and the energies of the pulses may be measured and compared with each other.

This may provide for an exact determination, whether a pulse sharing effect or a fluorescence photon generation has occurred.

According to another exemplary embodiment of the present invention, the coincidence detection and correction unit is parameterised by a set of thresholds.

For example, the set of thresholds may comprise the allowed time window for pulse sharing, the allowed time window for fluorescence, the threshold for the similarity measure to detect pulse sharing and the maximal energy for X-ray photons.

Furthermore, according to another exemplary embodiment of the present invention, the correction of the first detection data is performed on the basis of a priority assignment of coincidences.

These priorities may either be defined statically, dynamically or systematically by calculating a likelihood measure for each coincidence and selecting the coincidence with the highest likelihood.

According to another exemplary embodiment of the present invention, the first pulse and the second pulse correspond to electromagnetic radiation impinging on the detector unit.

In other words, the detector unit may be adapted for detecting single photons.

According to another exemplary embodiment of the present invention, the electromagnetic radiation is X-ray radiation. Furthermore, the detector unit may be used in connection with an examination apparatus for medical applications, such as a computer tomography examination apparatus or a rotational X-ray apparatus.

Furthermore, according to another exemplary embodiment of the present invention, the detector unit comprises a third detector cell adapted for detecting a third pulse, wherein the first, second and third detector cells have a shape such that a likelihood of a coincidence of the first and second pulses is bigger than a likelihood of a coincidence of the first and third pulses.

Therefore, a cell, which has four neighbouring cells may not need four CDC-units for the four neighbour cells. The number of CDC-units may be reduced to two for the neighbours at the larger sides of the detector cell.

Furthermore, according to another exemplary embodiment of the present invention, an examination apparatus with a detector unit for examination of an object of interest and for performing a coincidence detection and correction is provided, wherein the detector unit comprises a first detector cell adapted for detecting a first pulse resulting in first detection data and a second detector cell adapted for detecting a second pulse resulting in second detection data, and a coincidence detection and correction unit coupled to the first and second detector cells and adapted for detecting a coincidence of the first and second pulses, wherein the coincidence detection and correction unit is further adapted for performing a correction of the first detection data, if a coincidence is detected.

This may provide for an examination apparatus which provides a reduced degradation of measured signals.

According to another exemplary embodiment of the present invention, the examination apparatus is configured as one of the group consisting of a material testing apparatus, a baggage inspection apparatus and a medical application apparatus.

Furthermore, according to another exemplary embodiment of the present invention, the examination apparatus is adapted as one of a computed tomography apparatus and a rotational X-ray apparatus.

According to another exemplary embodiment of the present invention, a method of examination of an object of interest is provided, in which a first pulse is detected by a first detector cell, resulting in first detection data, and in which a second pulse is detected by a second cell, resulting in second detection data. Furthermore, a coincidence of the first and second pulses is detected, for example by a coincidence detection and correction unit coupled to the first and second detector cells. Furthermore, a correction of the first detection data is performed, if a coincidence is detected.

It should be noted in this context, that not only a correction of the first detection data may be performed, but also a correction of the second detection data, or vice versa. The form of the correction may depend on the quality of the detected coincidence event.

According to another exemplary embodiment of the present invention, a computer-readable medium is provided, in which a computer program for examination of an object of interest is stored which, when being executed by a processor, causes the processor to carry out the above-mentioned method steps.

Furthermore, according to another exemplary embodiment of the present invention, a program element for examination of an object of interest is provided, which, when being executed by a processor, causes the processor to carry out the above-mentioned method steps.

Both skilled in the art will readily appreciate that the method of examination of the object of interest may be embodied as the computer program, i.e. by software, or may be embodied using one or more special electronic optimization circuits, i.e. in hardware, or the method may be embodied in hybrid form, i.e. by means of software components and hardware components.

The program element according to an exemplary embodiment of the present invention is preferably loaded into working memories of a data processor. The data processor may thus be equipped to carry out embodiments of the methods of the present invention. The computer program may be written in any suitable programming language, such as, for example, C++ and may be stored on a computer-readable medium, such as a CD-ROM. Also, the computer program may be available from a network, such as the WorldWideWeb, from which it may be downloaded into image processing units or processors, or any suitable computers.

Furthermore, according to another exemplary embodiment of the present invention, an image processing or signal processing device for examination of an object of interest is provided, the signal processing device comprising a memory for storing a data set of the object of interest, the data set comprising first detection data relating to a first pulse and second detection data relating to a second pulse, wherein the signal processing device is adapted for detecting a coincidence of the first and second pulses and performing a correction of the first detection data, if a coincidence is detected.

It may be seen as the gist of an exemplary embodiment of the present invention that a dedicated coincidence detection and correction method is used to reduce the effects of pulse sharing and fluorescence induced crosstalk. A detector unit according to an exemplary embodiment of the present invention may comprise a plurality of detector cells, wherein a coincidence detection and correction unit of a respective detector cell watches the signals detected at neighbouring cells. If there is a pulse at the same time in a neighbouring cell, the pulses are analyzed and a correction is applied to the data. The analysis of the pulses may be optimized with respect to the characteristics of the underlying physical effects.

These and other aspects of the present invention will become apparent from and elucidated with reference to the embodiments described hereinafter.

Exemplary embodiments of the present invention will be described in the following, with reference to following drawings.

The illustration in the drawings is schematic. In different drawings, similar or identical elements are provided with the same reference numerals.

FIG. 1 shows an exemplary embodiment of a computer tomography scanner system according to the present invention.

Figure 1:
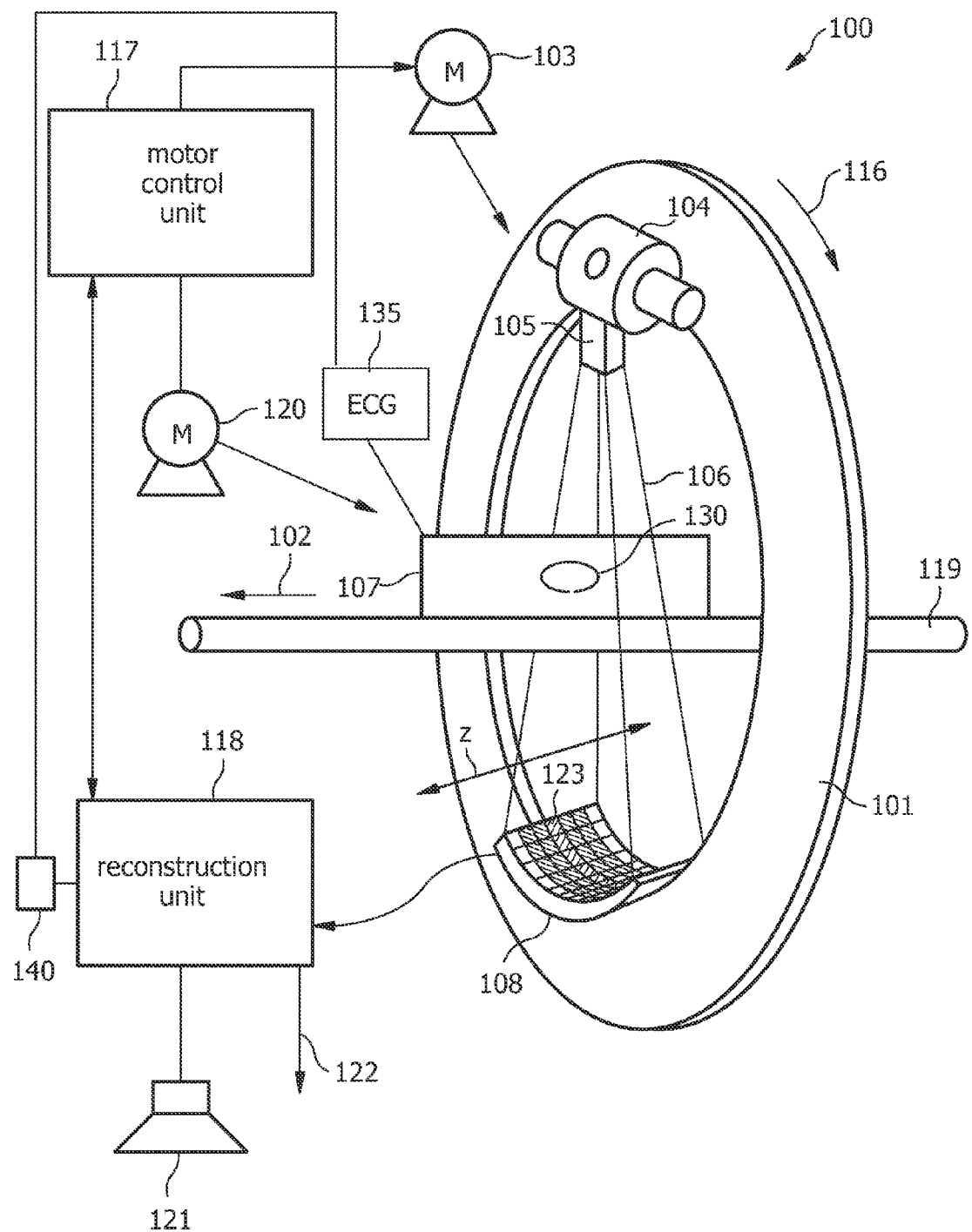
FIG. 1 shows a simplified schematic representation of a CT examination apparatus according to an exemplary embodiment of the present invention.

The computer tomography apparatus 100 depicted in FIG. 1 is a cone-beam CT scanner. However, the invention may also be carried out with a fan-beam geometry. In order to generate a primary fan-beam, the aperture system 105 can be configured as a slit collimator.

The CT apparatus depicted in FIG. 1 comprises a gantry 101, which is rotatable around a rotational axis 102. The gantry 101 is driven by means of a motor 103. Reference numeral 104 designates a source of radiation such as an X-ray source, which, according to an aspect of the present invention, emits polychromatic or monochromatic radiation.

Reference numeral 105 designates an aperture system which forms the radiation beam emitted from the radiation source to a cone-shaped radiation beam 106. The cone-beam 106 is directed such that it penetrates an object of interest 107 arranged in the centre of the gantry 101, i.e. in an examination region of the CT scanner, and impinges onto the detector 108. As may be taken from FIG. 1, the detector 108 is arranged on the gantry 101 opposite to the source of radiation 104, such that the surface of the detector 108 is covered by the cone-beam 106. The detector 108 depicted in FIG. 1 comprises a plurality of detector elements 123 each capable of detecting X-rays which have been scattered by or passed through the object of interest 107.

The detector 108 is described below in greater detail, with respect to FIG. 2.

During scanning of the object of interest 107, the source of radiation 104, the aperture system 105 and the detector 108 are rotated along the gantry 101 in the direction indicated by an arrow 116. For rotation of the gantry 101 with the source of radiation 104, the aperture system 105 and the detector 108, the motor 103 is connected to a motor control unit 117, which is connected to a reconstruction unit 118 (which may also be denoted as a calculation of determination unit).

In FIG. 1, the object of interest 107 is a human being which is disposed on an operation table 119. During the scan of, e.g., the heart 130 of the human being 107, while the gantry 101 rotates around the human being 107, the operation table 119 displaces the human being 107 along a direction parallel to the rotational axis 102 of the gantry 101. By this, the heart 130 is scanned along a helical scan path. The operation table 119 may also be stopped during the scans to thereby measure single slices. It should be noted that in all of the described cases it is also possible to perform a circular scan, where there is no displacement in a direction parallel to the rotational axis 102, but only the rotation of the gantry 101 around the rotational axis 102.

Moreover, an electrocardiogram device 135 may be provided which measures an electrocardiogram of the heart 130 of the human being 107 while X-rays attenuated by passing the heart 130 are detected by detector 108. The data related to the measured electrocardiogram are transmitted to the reconstruction unit 118.

The detector 108 is connected to the reconstruction unit 118. The reconstruction unit 118 receives the detection result, i.e. read-outs from the detector element 123 of the detector 108 and determines a scanning result on the basis of these read-outs. Furthermore, the reconstruction unit 118 communicates with the motor control unit 117 in order to coordinate the movement of the gantry 101 with motors 103 and 120 with the operation table 119.

The reconstruction unit 118 may be adapted for reconstructing an image from read-outs of the detector 108. The reconstructed image generated by the reconstruction unit 118 may be output to a display (not shown in FIG. 1) via an interface 122.

The reconstruction unit 118 may be realized by a data processor to process read-outs from the detector element 123 of the detector 108.

Furthermore, as may be taken from FIG. 1, the calculation unit may be connected to a loudspeaker 121 to automatically output an acoustic signal.

The measured data, namely the cardiac computer tomography data and electrocardiogram data are processed by the reconstruction unit 118 which may be further controlled via a graphical user-interface 140. This retrospective analysis may be based on helical cardiac cone-beam reconstruction scheme using retrospective ECG gating. It should be noted, however, that the present invention is not limited to the specific data acquisition and construction.

Figure 2:
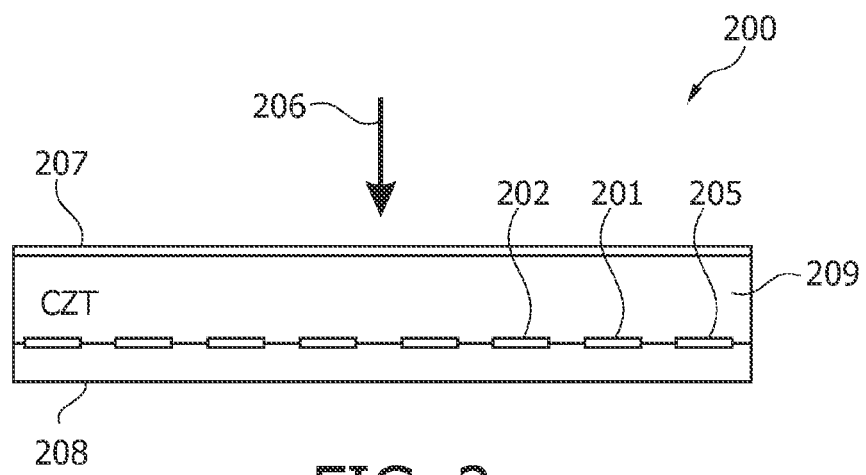
FIG. 2 shows a simplified schematic representation of a CZT detector.

FIG. 2 shows a simplified schematic representation of a CZT detector 200, which may be implemented in a CT examination apparatus, such as detector 108 of FIG. 1.

The detector 200 comprises a substrate 208 and a cadmium/zinc/tellurium (CZT) layer 209. Furthermore, a cathode 207 and an anode array, comprising anodes or detector cells 201, 202, 205 are provided.

Incoming photons 206 interact with the CZT 209 and generate an electron cloud. A strong electrical field between the top layer 207 and the bottom layer 208 accelerate this cloud towards the lower electrodes 201, 202, 205. The related pulse is detected and counted. The pulse height may allow the detection of the energy of the photon.

Figure 3:
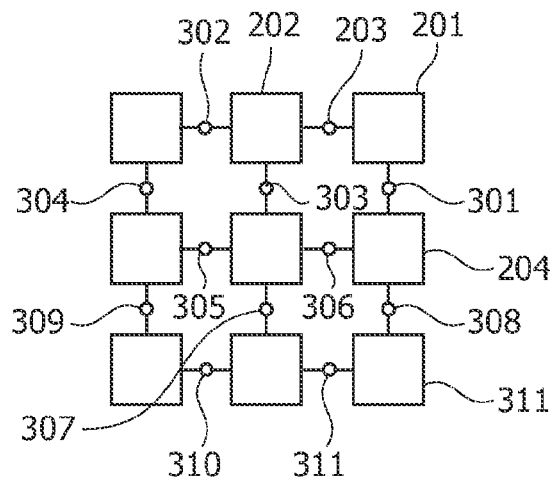
FIG. 3 shows a simplified schematic representation of a detector geometry according to an exemplary embodiment of the present invention.

FIG. 3 shows a simplified schematic representation of a detector geometry. The detector unit depicted in FIG. 3 comprises 9 detector cells, such as detector cells 201, 202. Furthermore, the detector unit comprises twelve coincidence detection and correction units, i.e. CDC-units 203 and 301-311. it should be noted, that a detector unit according to the invention may comprise many more detector cells and CDC-units.

As may be seen from FIG. 3, each detector cell has a CDC-unit which couples the cell to a neighbouring cell. Therefore, a coincidence detection is realized in such a way that the electronics of each detector cell watches the signals detected in the neighbouring cells. If there is a pulse at the same time in a neighbour cell, the pulses can be analyzed and a correction can be applied to the data. The analysis of the pulses may be optimized with respect to the characteristics of the underlying physical effects. Such specific characteristics are, for example, that the two pulses of a pulse sharing event appear at the very same time and have a very similar pulse shape but perhaps different amplitudes. In fluorescence one may know very precisely the possible set of energies for the fluorescence event. As an example, if a CZT detector is used the fluorescence energies of cadmium and tellurium are known.

It should be noted that the coincidence detection and correction according to the invention may be realized with analogous or digital components (or a mixture thereof). A description of the coincidence detection and correction is given below by means of an algorithmic specification independent of the hardware realization. A respective coincidence detection and correction unit may be placed between every two neighbouring cells for which a coincidence is expected. For example, each detector cell generates two measures per incoming pulse. These measures include the time t of the event and the energy e of the event. Furthermore, the CDC-unit comprises a measuring device for measuring the similarity of the pulse shape of the two neighbour cells. In addition to the measures ($t_1$, $t_2$, $e_1$, $e_2$) the CDC-unit is parameterized by a set of thresholds.

Four exemplary thresholds are:
$T_1$, i.e. the allowed time window for pulse sharing, $T_2$, i.e. the allowed time window for fluorescence, $T_s$, i.e. the threshold for the similarity measure to detect pulse sharing, and $T_e$, i.e. the maximal energy for X-ray photons.

It may happen that two individual X-ray photons hit two neighbouring cells at about the same time. In this case care may have to be taken not to treat these events as pulse sharing or fluorescence. The parameter and threshold may be defined such that the advantage of coincidence detection and correction out performs the disadvantages by false-positive detection or indirect limitation of the count-rate capabilities.

In case a cell detects coincidences with more than one neighbour, priorities may be assigned to specific coincidences. These priorities may either be defined statically (e.g. a coincidence with the right neighbour has a higher priority than a coincidence with the left neighbour), dynamically (e.g. alternating priority, random choice) or systematically by calculating a likelihood measure for each coincidence and selecting the coincidence with the highest likelihood.

In order to minimize the effort for building and arranging the CDC-units by keeping them simple and by minimizing the number of CDC-units, optimized cell geometries may be implemented. A conventional detector cell geometry may use squared electrodes, as depicted in FIG. 3.

Figure 4:
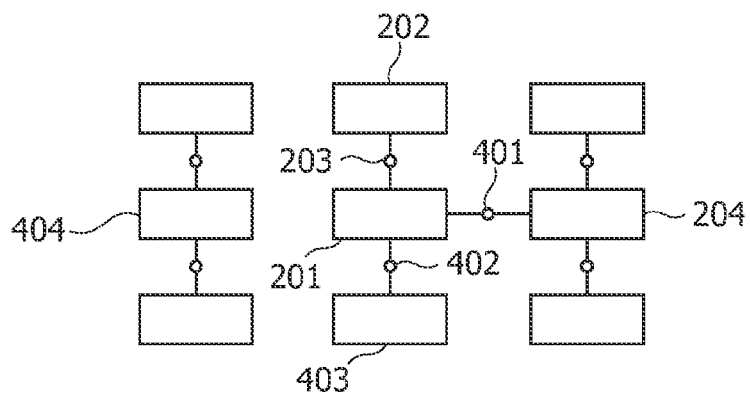
FIG. 4 shows a simplified schematic representation of a detector geometry according to another exemplary embodiment of the present invention.

FIG. 4 shows a schematic representation of a cell geometry according to another exemplary embodiment of the present invention. Here, the detector cells, such as detector cells 201, 202, 204, are adapted in the form of rectangular electrodes having the same area as the squared electrodes of FIG. 3. Therefore, the likelihood of pulse sharing and fluorescence is reduced for the neighbours 404, 204 at the smaller sides of the detector cell 201. In such a design, the number of CDC-units 203, 402 may be reduced to two units for the neighbours 202, 403 at the larger sides. Consequently, a CDC-unit 401 may no longer be necessary.

It should be noted that the proposed CDC scheme may also be applied to other geometries than those shown with respect to FIGS. 3 and 4.

Figure 5:
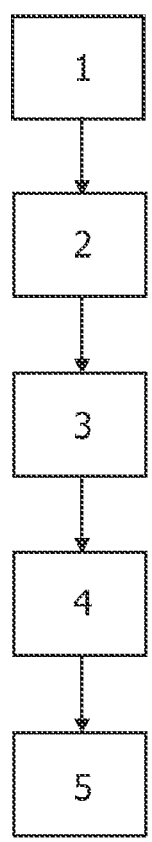
FIG. 5 shows a flow-chart of an exemplary method according to the present invention.

FIG. 5 shows a flow-chart of a method according to an exemplary embodiment of the present invention. The method starts at step 1 with the emission of electromagnetic radiation by a radiation source. Then, in step 2, a first pulse which results in first detection data is detected by a first detector cell. More or less at the same time, a second pulse is detected by a second detector cell, resulting in second detection data (step 3). Then, in step 4, a coincidence of the first and second pulses is detected by the coincidence detection and correction unit connected to the first and second detector cells.

If the similarity measure of the pulses exceeds a threshold ($T_s$) and the absolute difference of the pulse times ($t_1$, $t_2$) is lower than a threshold ($T_1$) and the sum of the energy of the pulses ($e_1$, $e_2$) does not exceed a threshold ($T_e$) than pulse sharing is assumed.

If the absolute difference of the pulse times ($t_1$, $t_2$) is lower than a threshold ($T_2$) and $e_1$ or $e_2$ corresponds to one of the assumed fluorescence energy levels and the sum of the energy of the pulses ($e_1$, $e_2$) does not exceed a threshold ($T_e$) then fluorescence is assumed.

If a coincidence is detected (either pulse sharing or fluorescence) and the coincidence has the highest priority, the measures of the two cells are corrected in step 5. The correction consists of:

a) not counting the event in one cell, and
b) counting the event with an energy level of $e_1+e_2$ in the other cell.

The question which cell has to be corrected according to which correction scheme may either be defined statically or dynamically (e.g. alternating or random).

Figure 6:
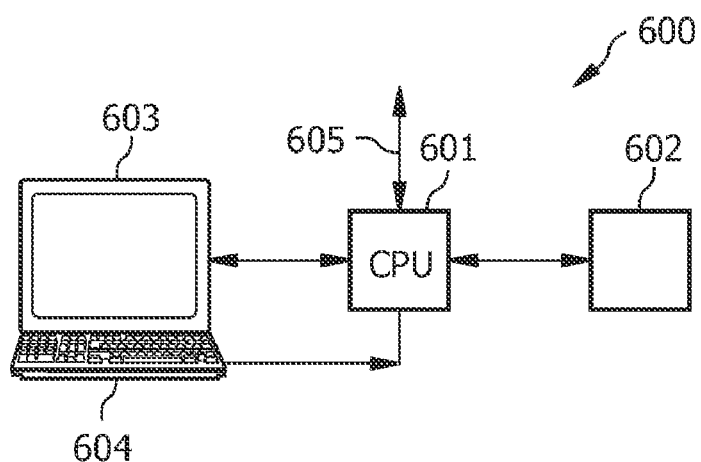
FIG. 6 shows an exemplary embodiment of a processing device according to the present invention, for executing an exemplary embodiment of a method in accordance with the present invention.

FIG. 6 shows an exemplary embodiment of a data processing device 600 according to the present invention for executing an exemplary embodiment of a method in accordance with the present invention.

The data processing device 600 depicted in FIG. 6 comprises a central processing unit (CPU) or signal processor, such as an image processor 601 connected to a memory 602 for storing detection data acquired by a detector unit and representing an object of interest, such as a patient or an item of baggage. The data processor or image processor 601 may be connected to a plurality of input/output network or diagnosis devices, such as a CT device. The data processor 601 may furthermore be connected to a display device 603, for example, a computer monitor, for displaying information or an image computed or adapted in the data processor 601. An operator or user may interact with the data processor 601 via a keyboard 604 and/or other output devices, which are not depicted in FIG. 6.

Furthermore, via the bus system 605, it may also be possible to connect the signal processing and control processor 601 to, for example, a motion monitor, which monitors a motion of the object of interest. In case, for example, a lung of a patient is imaged, the motion sensor may be an exhalation sensor. In case the heart is imaged, the motion sensor may be an electrocardiogram.

Exemplary embodiments of the invention may be sold as a software option to CT scanner console, imaging workstations or PACS workstations.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. Detector unit for performing a coincidence detection and correction, the detector unit comprising:
    a first detector cell adapted for detecting a first pulse resulting in first detection data and a second detector cell adapted for detecting a second pulse resulting in second detection data;
    a third detector cell adapted for detecting a third pulse;
    wherein the first, second and third detector cells have a shape such that a likelihood of a coincidence of the first and second pulses is bigger than a likelihood of a coincidence of the first and third pulses; and
    a coincidence detection and correction unit coupled to the first and second detector cells and adapted for detecting a coincidence of the first and second pulses;
    wherein the coincidence detection and correction unit is further adapted for performing a correction of the first detection data, if a coincidence is detected.

2. The detector unit of claim 1,
    wherein the detection of the coincidence is performed on the basis of an analysis of the first and second detection data.

3. The detector unit of claim 2,
    wherein the first detector cell is adapted for generating a first measure and a second measure corresponding to the first pulse;

wherein the first measure corresponds to a first time of the first pulse and wherein the second measure corresponds to a first energy of the first pulse;
wherein the second detector cell is adapted for generating a third measure and a fourth measure corresponding to the second pulse;
wherein the third measure corresponds to a second time of the second pulse and wherein the fourth measure corresponds to a second energy of the second pulse;
wherein the analysis is performed on the basis of the first, second, third and fourth measure.

4. The detector unit of claim 2,
wherein the analysis is adapted for determining whether a pulse sharing event or a fluorescence photon generation event has occurred.

5. The detector unit of claim 1,
wherein the coincidence detection and correction unit is parameterised by a set of thresholds; and
wherein the correction of the first detection data is performed on the basis of the parameterisation.

6. The detector unit of claim 1,
wherein the first pulse and the second pulse correspond to electromagnetic radiation impinging on the detector unit.

7. The detector unit of claim 6,
wherein the electromagnetic radiation is x-ray radiation.

8. The detector unit of claim 1,
wherein the detector unit is adapted for a computed tomography examination apparatus.

9. A detector unit for performing a coincidence detection and correction, the detector unit comprising:
a first detector cell adapted for detecting a first pulse resulting in first detection data and a second detector cell adapted for detecting a second pulse resulting in second detection data; and
a coincidence detection and correction unit coupled to the first and second detector cells and adapted for detecting a coincidence of the first and second pulses;
wherein the coincidence detection and correction unit is further adapted for performing a correction of the first detection data, if a coincidence is detected,
wherein the correction of the first detection data is performed on the basis of a priority assignment of coincidences, and
wherein the priority assignment is performed on the basis of a likelihood measure for each coincidence and a selection of a coincidence with the highest likelihood.

10. The unit of claim 9, where the priority assignment is defined statically.

11. The unit of claim 9, where the priority assignment is defined dynamically.

12. Examination apparatus with a detector unit for examination of an object of interest and for performing a coincidence detection and correction, the detector unit comprising:
a first detector cell adapted for detecting a first pulse resulting in first detection data and identifying a detection time of the first pulse detection;
a second detector cell adapted for detecting a second pulse resulting in second detection data and identifying a detection time of the second pulse detection; and
a coincidence detection and correction unit coupled to the first and second detector cells and adapted for detecting a coincidence of the first and second pulses, wherein the coincidence is detected, at least in part, by evaluating an absolute difference of the detection time of the first pulse detection and the detection time of the second pulse detection; wherein the coincidence detection and correction unit is further adapted for:
determining if the first detection data or if the second detection data should be corrected in response to detecting the coincidence;
performing a correction of the first detection data in response to determining that the first detection data should be corrected; and
performing a correction of the second detection data in response to determining that the second detection data should be corrected.

13. The examination apparatus of claim 12, the examination apparatus being configured as one of the group consisting of a material testing apparatus, a baggage inspection apparatus, a medical application apparatus and a micro CT system.

14. The examination apparatus of claim 12, the examination apparatus being adapted as one of a computed tomography apparatus and a rotational X-ray apparatus.

15. The apparatus of claim 12, wherein determining if the first detection data or if the second detection data should be corrected comprises:
selecting the first detection data if a closest in time previous correction corrected the second detection data; and
selecting the second detection data if the closest in time previous correction corrected the first detection data.

16. The method of claim 12, wherein determining if the first detection data or if the second detection data should be corrected comprises:
randomly selecting the first detection data or the second detection data for correction.

17. A method of examination of an object of interest with an examination apparatus, method comprising the steps of:
detecting, by a first detector cell, a first pulse resulting in first detection data;
detecting, by a second detector cell, a second pulse resulting in second detection data;
detecting a coincidence of the first and second pulses;
determining if the first detection data or if the second detection data should be corrected in response to detecting the coincidence of the first and second pluses;
performing a correction of the first detection data, if a coincidence is detected in response to determining that the first detection data should be corrected; and
performing a correction of the second detection data in response to determining that the second detection data should be corrected.

18. The method of claim 17, wherein determining if the first detection data or if the second detection data should be corrected comprises:
randomly selecting the first detection data or the second detection data for correction.

19. The method of claim 17, wherein determining if the first detection data or if the second detection data should be corrected comprises:
selecting the first detection data if a closest in time previous correction corrected the second detection data; and
selecting the second detection data if the closest in time previous correction corrected the first detection data.

* * * * *